United States Patent
Anapliotis

(10) Patent No.: US 10,568,671 B2
(45) Date of Patent: Feb. 25, 2020

(54) IMPLANTABLE COMPENSATING SLEEVE FOR AN ENDOPROSTHESIS

(71) Applicant: Merete Holding GmbH, Berlin (DE)

(72) Inventor: Emmanuel Anapliotis, Berlin (DE)

(73) Assignee: Merete Holding GmbH, Berlin (DE)

( * ) Notice: Subject to any disclaimer, the term of this patent is extended or adjusted under 35 U.S.C. 154(b) by 0 days.

(21) Appl. No.: 16/081,110

(22) PCT Filed: Mar. 27, 2017

(86) PCT No.: PCT/DE2017/000084
§ 371 (c)(1),
(2) Date: Aug. 30, 2018

(87) PCT Pub. No.: WO2017/167324
PCT Pub. Date: Oct. 5, 2017

(65) Prior Publication Data
US 2019/0090919 A1   Mar. 28, 2019

(30) Foreign Application Priority Data
Mar. 29, 2016  (DE) .......... 10 2016 003 837

(51) Int. Cl.
*A61B 17/72* (2006.01)
*A61B 17/58* (2006.01)
(Continued)

(52) U.S. Cl.
CPC ........ *A61B 17/7283* (2013.01); *A61F 2/3662* (2013.01); *A61F 2002/30535* (2013.01); *A61F 2002/3668* (2013.01)

(58) Field of Classification Search
CPC ... A61B 17/7283; A61B 17/72; A61B 17/164; A61B 17/7241; A61B 17/921;
(Continued)

(56) References Cited

U.S. PATENT DOCUMENTS 3,977,398 A * 8/1976 Burstein ................ A61B 17/72
606/62
8,668,692 B1 * 3/2014 Lindvall ................ A61B 17/72
606/62
(Continued)

FOREIGN PATENT DOCUMENTS

DE    1805665    5/1970
DE    3909182    8/1990
(Continued)

OTHER PUBLICATIONS

International Search Report, PCT/DE2017/000084, dated Aug. 30, 2017.
Written Opinion, PCT/DE2017/000084, dated Aug. 30, 2017.

*Primary Examiner* — Pedro Philogene
(74) *Attorney, Agent, or Firm* — Andrus Intellectual Property Law, LLP

(57) ABSTRACT

An implantable compensating sleeve is applied between an oblong implant section of a first implant, and a second implant that encloses the oblong implant section of said first implant. The compensating sleeve has a sheath having a sheath body and a passage, running from the proximal to the distal end of the sheath body, for receiving said oblong implant section of the first implant. The sheath body is divided, by slits which cut into the sheath body in the longitudinal direction and originate alternately from the distal and from the proximal edge of the sheath body, into meander-like segments each comprising two longitudinal arms. The sheath body is radially expandable in at least one subsection. On the inner surface of the sheath body facing the passage, at least one bulge extends in the longitudinal direction of a meander-like segment, forming an inner profile that protrudes into the passage.

10 Claims, 4 Drawing Sheets

(51) Int. Cl.
*A61B 17/68* (2006.01)
*A61F 2/36* (2006.01)
*A61F 2/30* (2006.01)

(58) Field of Classification Search
CPC ................. A61F 2/3662; A61F 2/3676; A61F 2002/3668; A61F 2002/30535
USPC ......................... 606/62–68; 623/22.11–22.12, 623/22.4–22.46, 23.15–23.38
See application file for complete search history.

(56) References Cited

U.S. PATENT DOCUMENTS

| | | |
|---|---|---|
| 2004/0230193 A1 | 11/2004 | Cheung et al. |
| 2008/0255560 A1 | 10/2008 | Myers et al. |
| 2008/0269745 A1 | 10/2008 | Justin |
| 2011/0238121 A1 | 9/2011 | Watanabe et al. |
| 2011/0306975 A1 | 12/2011 | Kaikkonen et al. |
| 2014/0350691 A1 | 11/2014 | Linares et al. |

FOREIGN PATENT DOCUMENTS

| | | |
|---|---|---|
| DE | 102005054708 | 5/2007 |
| DE | 102008062226 | 8/2009 |
| EP | 0761175 | 3/1997 |
| JP | 2955701 | 7/1999 |

\* cited by examiner

IMPLANTABLE COMPENSATING SLEEVE FOR AN ENDOPROSTHESIS

CROSS-REFERENCE TO RELATED APPLICATIONS

This application is the U.S. national stage application of International Application PCT/DE2017/000084, filed Mar. 27, 2017, which international application was published on Oct. 5, 2017, as International Publication WO 2017/167324 in the German language. The International Application claims priority of German Patent Application No. 10 2016 003 837.3, filed Mar. 29, 2016. The international application and German application are both incorporated herein by reference, in entirety.

The present invention refers to an implantable compensating sleeve for an endoprosthesis, in particular a recumbent (lying already in place) endoprosthesis for the intramedullary care of a periprosthetic or interprosthetic fracture.

BACKGROUND OF THE INVENTION

Due to the high number of implanted hip and knee prostheses at an increasing age of the operated patients, the frequency of periprosthetic or interprosthetic fractures is increasing.

Periprosthetic fractures are fractures in the area of a prothesis and are often caused by a fall. Also, a low bone quality due to osteoporotic or osteolytic modifications may lead to a periprosthetic fracture.

Interprosthetic fractures occur between two implants or prosthesis inserted in the same bone. Interprosthetic fractures are most often found in the femur between a hip and a knee prosthesis.

Depending on the kind and profile of a fracture, its location with respect to the prosthesis and the dependence on the seating stability of the prothesis, various therapy forms are indicated.

In particular, in order to choose the type of fracture care, it is decisive, whether the seating of the prothesis has come loose. If the prothesis is still solidly anchored to the bone, in most cases a revision of the prosthesis may be omitted.

The standard method for the treatment of periprosthetic or interprosthetic fractures, which are categorized as type B1 according to the Vancouver classification, is represented by the angularly stable plate osteosynthesis. However, the treatment by plate osteosynthesis is responsible for the weakening of the prosthetically treated bone due to formation of predetermined breaking points, in the area of which successive fractures may occur. Depending on the specific requirements the use of a megaprosthesis as a complete femur insert may then be inevitable.

If the bone structure does not allow an osteosynthesis, the intramedullary stabilization represents an alternative operational technique, in which the defect is bridged by means of an individually manufactured interposition-nail.

Interposition nails offer a high stability and are manufactured in different sizes.

In case of fractures of type Vancouver B1, in which despite the fracture the hip or knee prosthesis is still solidly anchored to the bone, a further care method may be used, in which the implanted prosthesis may remain within the body. In this operational technique, for example, in order to bridge the bone defect in the femur, the shaft of an implanted hip prosthesis is connected to a femur nail, which is inserted distally into the medullar channel, by means of a sleeve-like intermediate module, whereby the shaft may be mechanically extended. This methodology has various advantages. On one hand, the duration and depth of the surgical intervention may be considerably reduced, and on the other hand, an improved healing and higher stability of the prosthetically treated bone may be considered, with a simultaneous reduction of the complication rate.

However, only a few modular endoprosthetic systems are available, in which the implant or prosthesis components are fitted to each other in a way that an already implanted prosthesis may be endoprosthetically expanded in a stable way in the course of a subsequent operation.

It is often the case that both the origin of a prosthesis shaft and its geometry and consistency may be univocally determined only when it has been operatively exposed. The surgeon then has to make a rapid assessment regarding whether a prepared endoprosthetic system is compatible with the pre-existing shaft and whether the subsequently implanted endoprosthetic system may be connected to the shaft end in a rotationally stable way.

The market for medical products offers a large variety of hip and knee prostheses, the configuration and size of which are clearly differentiated from each other. The fundamental differences are in particular in the length and in the cross-sectional profile of the prosthetic shafts and in their respective superficial texture. Some prostheses are provided, among other things, with corrugations or longitudinally extending groove profiles, which hinder an intramedullary expansion to an endoprosthesis due to an insufficient force fit between the prosthetic parts.

Endoprosthetic connection systems are known in the art which allow an endoprosthetic extension of exposed shaft ends after a periprosthetic fracture.

DE 10 2008 062 226 A1 discloses an extension of a proximal femur nail. The extension in the form of a distal femur nail, which may be inserted into the medullar space of the femur in a retrograde way, has a receiving opening at a proximal end, which opening may be slid over the distal end of the proximal femur nail. The securing occurs by means of a locking screw, which is additionally connected to the femur.

U.S. Pat. No. 8,668,692 B1 described a periprosthetic endoprosthetic system for an already implanted prosthesis shaft. This endoprosthetic system comprises a connection part, which has a longitudinal tripartite channel. The proximal area of this channel is provided for receiving the inner shaft end and adapted to the conical shaft shape. The connection between the inner shaft end and the conically shaped channel region occurs through force fit, with or without an additional cementing of the shaft end. In the distal end region of the channel a further implant may be screwed in for an endoprosthetic extension.

DE 39 09 182 C1 is also cited as a correlated state of the art.

SUMMARY OF THE INVENTION

The object of the invention is to provide an implantable supplemental component for an endoprosthetic extension of an inner (inside-lying) implant, with which, in order to avoid a revision of the inner (inside-lying) implant, the force fit between the inner (inside-lying) implant and an endoprosthetic extension may be improved in such a way that a rotationally stable connection between the inner (inside-lying) implant and the endoprosthetic extension may be achieved.

This object is achieved with an implantable compensating sleeve for an endoprosthesis, which is adapted for application between an oblong implant section of a first implant, and a second implant that encloses the longitudinal implant section of said first implant. The compensating sleeve takes the form of a sheath having a sheath body and a passage, running all the way from the proximal to the distal end of the sheath body, for receiving said oblong implant section of the first implant. The sheath body is divided, by means of slits which cut into the sheath body in the longitudinal direction and extend, alternately from the distal and from the proximal edge of the sheath body, into meander-like segments, each comprising two longitudinal arms. The sheath body is radially expandable in at least one subsection thereof. The compensating sleeve is characterized in that on the inner surface of the sheath body facing the passage, at least one bulge is provided, which extends in the longitudinal direction of a meander-like segment forming an inner profile that protrudes into the passage.

The inventive compensating sleeve is characterized in that due to its deformability, it may be flexibly adapted to a pre-existing cross-sectional shape of a shaft or nail, which represent a first inner implant. Due to the inner longitudinal bulges, a pre-existing groove profile may be compensated and thus an increased contact surface for a rotationally stable endoprosthetic expansion may be formed.

The term "first implant" in particular refers to hip prostheses, knee prostheses or shoulder prostheses as well as to femoral, tibial and Gamma nails or in general to bone nails which are inserted into the bone marrow. In particular, the term "first implant" refers to inner implants.

The term "oblong implant section" refers on one hand to a prosthetic shaft, in particular the end region which is anchored to the bone, of a prosthetic shaft, and on the other hand to a nail end region of a bone nail.

The term "second implant" refers to an implant, which is adapted for connection with the oblong implant section of the first implant, in that the oblong implant section of the first implant is introduced into a sheath-like receiving device in the second implant and is fixed therein by force fit.

The constructive differences between the first implant and the second implant may be compensated by applying the inventive compensating sleeve onto the end section of the first implant, whereby the surgeon is able to either obtain a coupling of the first and the second implant and/or to considerably increase the seating resistance of the composite between both implants in such a way that the required rotational stability is obtained.

The slits formed in the sheath body for forming the meander-like shape originate, alternately, from the distal end and from the proximal end and extend in opposite directions linearly in the longitudinal direction of the sheath body. The slits extend advantageously into the edge region of the opposite edge, whereby in the proximal edge region first transverse webs and in the distal edge region second transverse webs are formed. Only for the sake of definition, it is specified that the first transverse webs connect two adjacent longitudinal arms to form a longitudinal arm pairing of a meander-like segment and the second transverse webs connect two adjacent meander-like segments to each other.

In an advantageous embodiment, the longitudinal arms of a meander-like segment or of all meander-like segments are parallel to each other. In another embodiment, the slits may be formed in a zigzag shape or a curved shape.

In a further embodiment, the width of a first and/or second transverse web corresponds to the width of an adjacent longitudinal arm. All longitudinal arms advantageously have the same width.

By splitting the sheath body into meander-like segments, at least in a partial region of the sheath body an extensibility in the radial direction is obtained, whereby the sheath may be widened and may be slid on an oblong implant section of a first implant, by providing a clamping effect.

Due to the flexible shape of the sheath body subdivided into meander-like segments, the compensating sleeve may adapt, while sliding onto the oblong implant section of a first implant, to almost any cross-sectional shape and cross-sectional profile of the oblong implant section, so that it may be compatible with differently shaped shaft tips or nail ends.

The bulge extending on the inner side of the sheath body in the longitudinal direction of a meander-like segment is configured for engaging in a groove extending in the longitudinal direction of the oblong implant section of a first implant. Due to the engagement of a bulge in a longitudinal groove in the first implant, an undesired rotation of the oblong implant section and of the compensating sleeve inserted thereon is prevented.

In an advantageous embodiment, the at least on bulge extending in the longitudinal direction of a meander-like segment, extends over the entire width of two adjacent longitudinal arms and over the slit positioned between both longitudinal arms of a meander-like segment. In this embodiment, the bulge is thus in a split configuration, advantageously divided in half.

Due to this embodiment, the bulge engaging in a longitudinal groove of the first implant may be expanded, so that by spreading the longitudinal arms supporting the bulge, the same may be pressed laterally against the groove wall, whereby, beside the clamping fit of the compensating sleeve, a second clamping force is generated within the groove and thus increases the stability of the seating of the compensating sleeve. In order to optimize the seating stability, the inner profile of the compensating sleeve may be configured in a complementary form with respect to the groove profile in the oblong implant section of the first implant.

In a further embodiment, the bulges provided on the inner surface of the sheath body facing the passage, form an inner circumferential profile, having an undulating form in the cross-section of the compensating sleeve, with wave peaks and troughs. In particular, in such an inner profile, a peak and/or a trough of the undulating inner profile extends, respectively, over two adjacent longitudinal arms of a meander-like segment, preferably the undulating inner profile is provided with an axial symmetry so with respect to the longitudinal axis of the compensating sleeve.

In order to increase the clamping effect, the slits extending in the longitudinal direction of the sheath body may be alternately provided on the bottom of a wave trough and on the crest of a wave peak.

The outer surface of the outer sleeve forms the contact surface required for obtaining a rotationally stable force fit with the second implant. The strength of the composite formed by both implants directly depends on the size of the contact surface and also on the roughness of the material. The larger the contact surface, the higher the adhesion friction, which opposes a rotation of the assembled implants.

In order to form the largest contact surface possible, the outer side of the sheath body formed by the outer surface of the longitudinal arms of a meander-like segment is advantageously unprofiled, i.e. it has a planar surface.

In another case, in which the second implant is also provided with an inner profile in the recess for the first implant, in order to improve the seating resistance, the outer surface of the compensating sleeve may be provided with an outer profile, which is compatible with the inner profile of the second implant.

In another embodiment, the wall thickness of the sheath body in its distal edge region may be thicker than in the opposite proximal edge region of the sheath body.

The wall thickening advantageously increases uniformly in the longitudinal direction of the sheath body. The longitudinally increasing wall thickness may be provided radially all around the entire sheath body or also only in the region of one or more meander-like segments of the sheath body.

With such an inventive compensating sleeve a fit difference between a first implant, which is tapered towards the implant tip, such as a shaft tapered in the distal direction of a hip prosthesis, and a cylindrically formed implant recess in the second implant may be compensated.

Suitable materials used for manufacturing an inventive compensating sleeve are in particular surgical steels, titan or titan alloys. The compensating sleeve may also be made of a biocompatible plastic material, in particular PEEK.

A set with a plurality of compensating sleeves having different average inner diameters and/or different inner profiles may also be conceived. In order to determine the relevant diameter on the oblong implant section of the first implant, the set may also comprise a measurement jig.

BRIEF DESCRIPTION OF THE DRAWINGS

The invention is explained in the following by means of an exemplary embodiment. In particular.

DETAILED DESCRIPTION OF THE INVENTION

Figure 1:
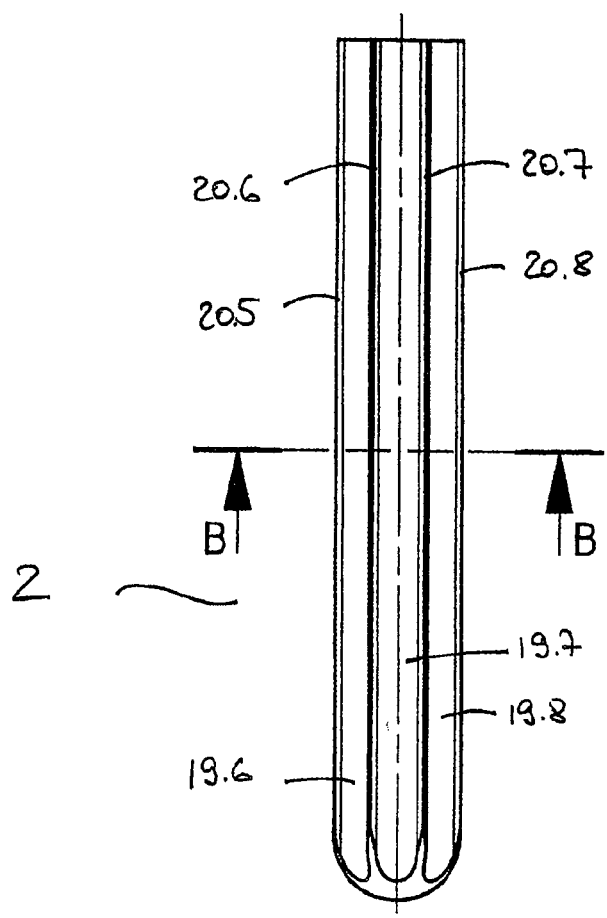
FIG. 1 shows a lateral and cross-sectional view of an oblong implant section of a first implant.
Figure 1:
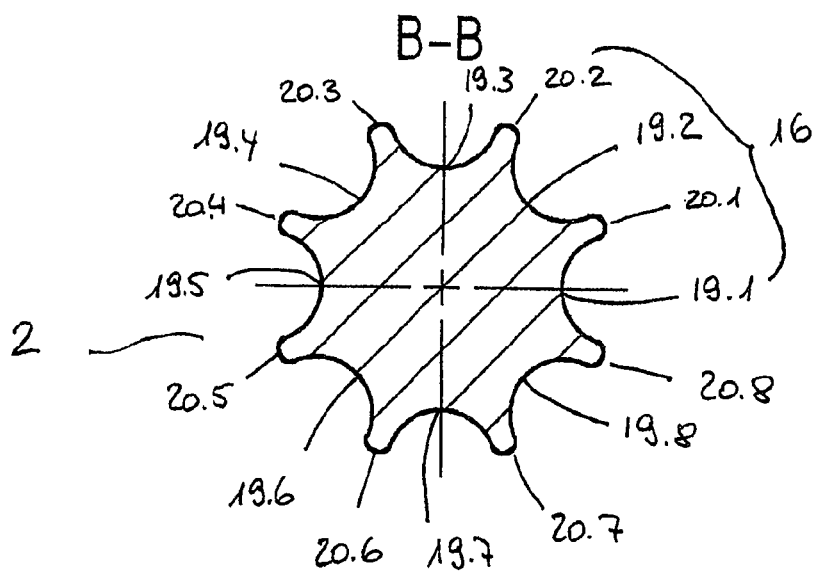

FIG. 1 shows both a lateral view and a cross-sectional view B-B of an oblong implant section of a first implant 2. The first implant 2 shown is a straight bone nail having a groove profile 16 which extends in the longitudinal direction. In FIG. 1, the nail end region 2 of the bone nail is shown, which has been operatively exposed, for example, after a periprosthetic fracture. As shown in cross-sectional view B-B, the undulating groove profile 16 is provided in the nail end region 2 of the bone nail with expanded wave troughs 19,1-19.8 having short pointed wave crests 20.1-20.8.

In order to provide a force-fit connection with a second implant having a smooth-walled receiving device, into which the nail end region 2 for an endoprosthetic expansion has to be inserted, only a very small contact surface is thus available for force transmission, since the contact may only be provided between the crests 20.1 to 20.8 and the wall of the receiving device (not shown).

Figure 2:
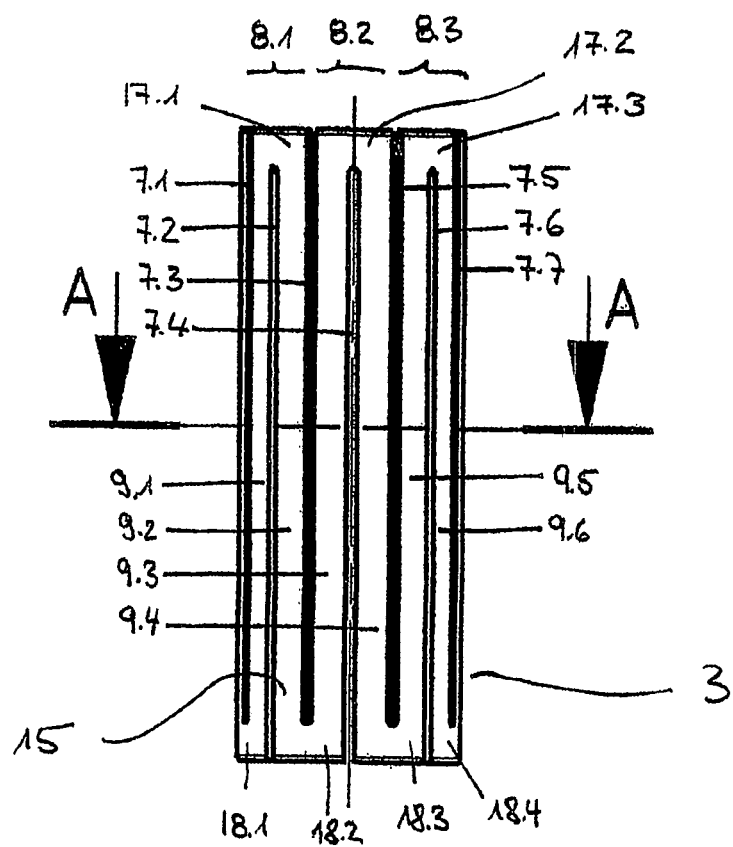
FIG. 2 shows a lateral view of an embodiment of an inventive compensating sleeve.
Figure 3:
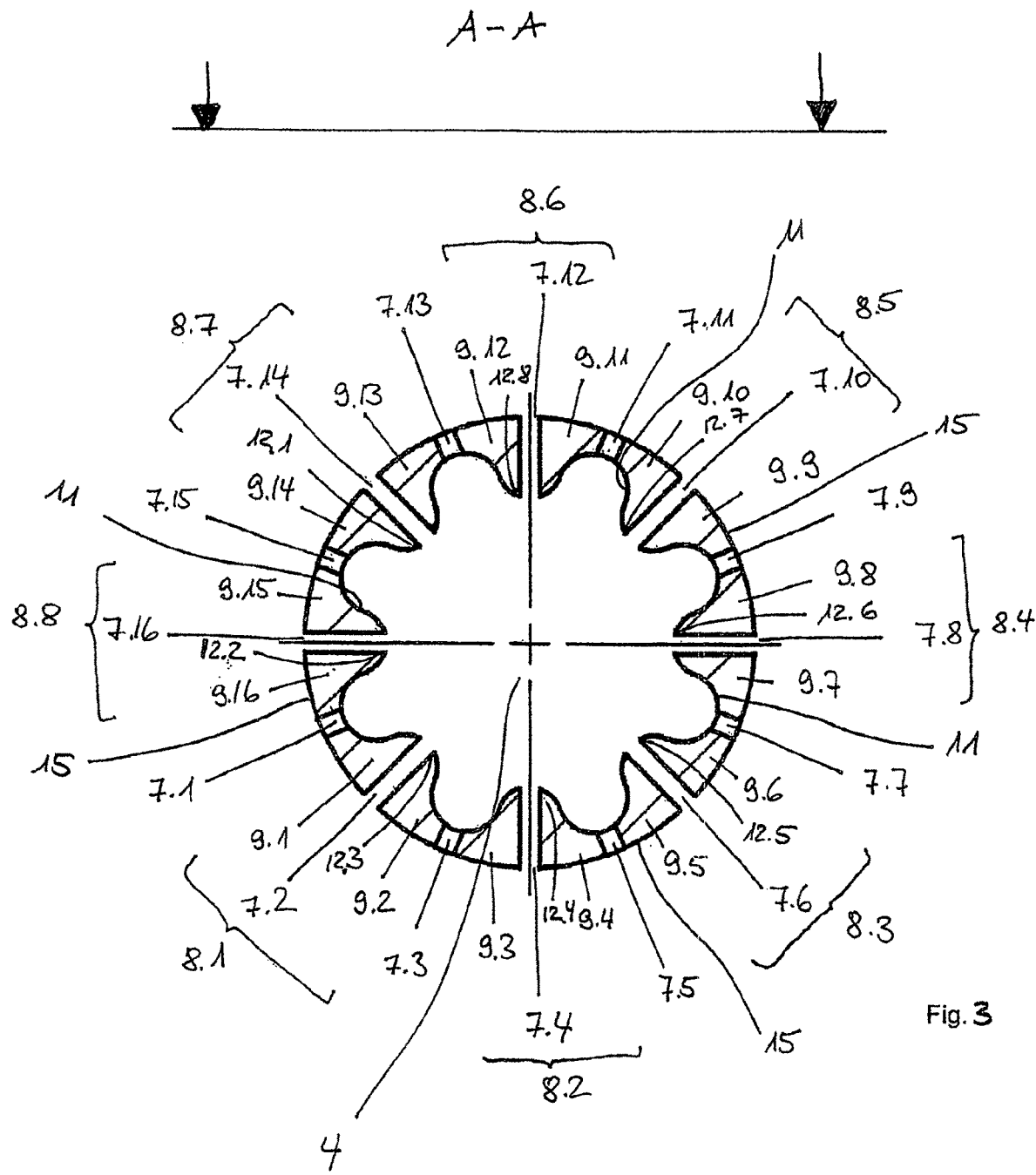
FIG. 3 shows a cross-sectional view of the embodiment of FIG. 2.

FIGS. 2 and 3 show an embodiment of the inventive compensating sleeve 1. FIG. 3 shows the cross-section A-A of FIG. 2.

The compensating sleeve 1 is composed of a sheath having a sheath body 3 and a passage 4 running all the way from the proximal end 6 to the distal end 5 of the sheath body for receiving the oblong implant section of the first implant 2.

The sheath body 3 is subdivided by means of slits 7.1 to 7.16 which cut into the sheath body 3 in the longitudinal direction and which originate alternately from the distal 5 and from the proximal edge 6 of the sheath body 3, into meander-like segments 8.1 to 8.8 each comprising two pairs of longitudinal arms 9.1-9.2. 9.3-9.4, 9.5-9.6, 9.7-9.8, 9.9-9.10, 9.11-9.12, 9.13-9.14, 9.15-9.16. Due to the provision of meander-like segments 8.1 to 8.8, the annular sheath body 3 may be expanded or widened over the entire length in a radial direction, in order to allow a snug and form-fitting insertion on the nail end 2.

The inner surface 10 facing the passage 4 of the sheath body 3 is profiled. The inner profile 11 is characterized by alternating wave peaks 13.1 to 13.8 and wave troughs 14.1 to 14.8. The undulating profile 11 is formed by bulges 12.1 to 12.8 provided on the inner surface 10 of the sheath body 3, which extend in the longitudinal direction of the sheath body 3 and extend in a circumferential direction over two pairs of longitudinal arms 9.1-9.2. 9.3-9.4, 9.5-9.6, 9.7-9.8, 9.9-9.10, 9.11-9.12, 9.13-9.14, 9.15-9.16.

Moreover, each bulge 12.1 to 12.8 extends over two respective adjacent longitudinal arms 9.1-9.2. 9.3-9.4, 9.5-9.6, 9.7-9.8, 9.9-9.10, 9.11-9.12, 9.13-9.14, 9.15-9.16 belonging to a meander-like segment 8.1 to 8.8.

Considering the undulating inner profile 11 as a whole, the peaks 13.1 to 3.8 and troughs 14.1 to 14.8 are configured in such a way that a peak 13.1 to 13.8 and/or a trough 14.1 to 14.8 of the undulating inner profile 11 runs over the entire width of a pair of longitudinal arms 9.1-9.2. 9.3-9.4, 9.5-9.6, 9.7-9.8, 9.9-9.10, 9.11-9.12, 9.13-9.14, 9.15-9.16 of a meander-like segment 8.1 to 8.8. Moreover, the undulating inner profile 11 is provided with an axial symmetry with respect to the longitudinal axis of the compensating sleeve 1.

The slits 7.1 to 7.16 provided in the longitudinal direction of the sheath body 3 extend in the longitudinal direction of the sheath body 3. They are linear and aligned in parallel to each other and are alternately provided on the bottom of a wave trough 14.1 to 14.8 and on a crest of a wave peak 13.1 to 13.8.

The slits 7.1 to 7.16 extend into the edge region of the opposite edge 5 or 6, whereby in the proximal edge region 6, first transverse webs 17 and in the distal edge region 5 second transverse webs 18 are formed, which respectively connect to each other two of the longitudinal arms 9. The first proximal transverse webs 16.1 to 16.8 and the second distal transverse webs 17.1 to 17.8 and the longitudinal arms 9.1 to 9.16 connected thereto have the same width.

In FIG. 2, in a front view of the sheath body 3, three meander-like segments 8.1, 8.2 and 8.3 are shown. Each meander-like segment 8.1, 8.2 or 8.3 is composed of a first transverse web 17.1, 17.2, 17.3 in the proximal edge region 6 and two adjacent pairs of longitudinal arms 9.1-9.2. 9.3-9.4, 9.5-9.6.

The adjacent meander-like segments 8.1, 8.2, 8.3 are connected to each other, annularly, through the second transverse webs 18.1, 18.2, 18.3 and 18.4 in the sheath body 3, which are provided on the side of the edge.

Figure 5:
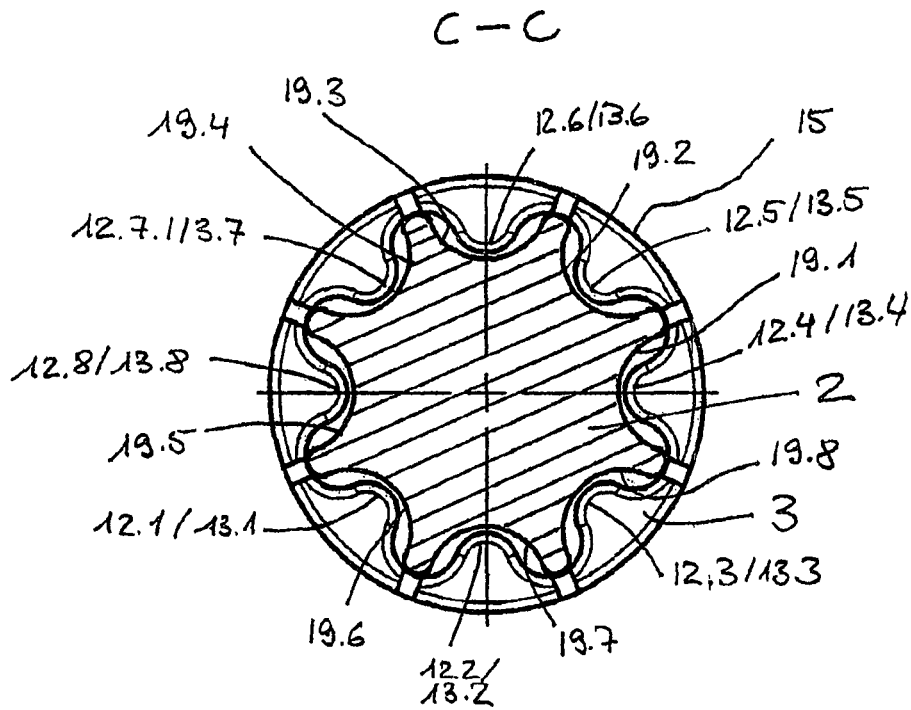
FIG. 5 shows a cross-sectional view of a compensating sleeve inserted on an oblong implant section of FIG. 1 according to FIG. 2.

As shown in FIG. 5, the undulating inner profile 11 is formed in a complementary way to the groove profile 16 in the oblong implant section of the first implant 2.

Figure 4:
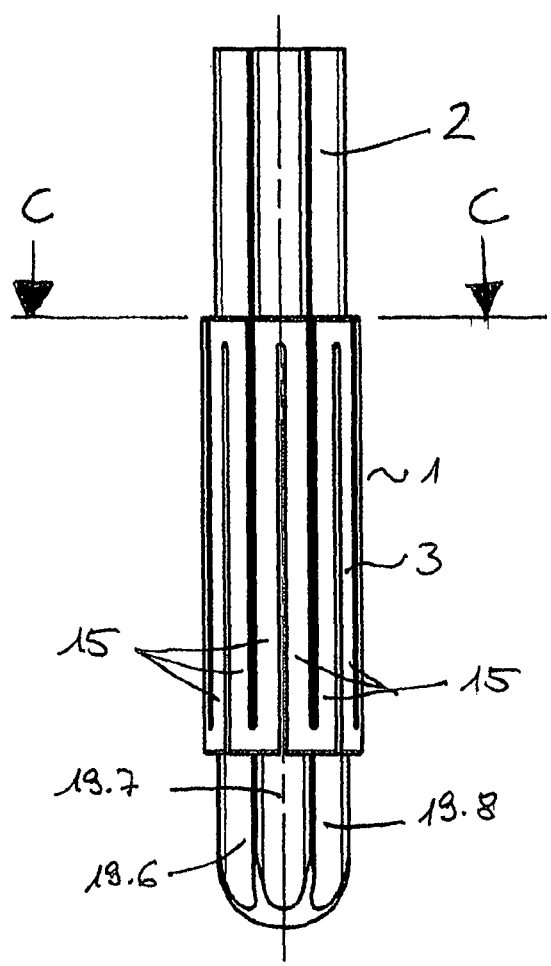
FIG. 4 shows a lateral view of a compensating sleeve inserted on an oblong implant section of FIG. 1 according to FIG. 2

FIGS. 4 and 5 show a compensating sleeve 1 inserted on the nail end region of a bone nail 2. When inserting the compensating sleeve 1, the sheath body 3 is expanded, whereby it fixedly and fittingly clamps on the end section 2 of the bone nail. The undulating inner profile 11 is composed of alternating peaks 13.1-13.8 and troughs 14.1-14.8. Each peak 13.1-13.8 forms a bulge 12.1-12.8, which extends in the longitudinal direction of the sheath body and which engages in a longitudinal groove (troughs 19.1-19.8 of groove profile 16) in the bone nail, so that the groove profile 16 is filled or compensated by inserting the compensating sleeve 1.

Due to the planar outer surfaces 15.1-15.16 of the longitudinal arms 9.1 to 9.16 of the meander-like segments 8.1 to 8.8 of sheath body 3, a planar outer face 15 is formed as a whole, which now provides a considerably larger contact surface with respect to the contact surface of the bone nail end 2, through which, in a force-fit with a second implant, which encloses the end section of the bone nail 2 in the region of the applied compensating sleeve 1, a rotationally stable endoprosthetic extension of the bone nail 2 may be achieved.

1 compensating sleeve for an endoprosthesis
2 oblong implant section of a first implant
3 sheath body
4 passage
5 distal edge region
6 proximal edge region
7 slit (7.1-7.16)
8 meander-like segment (8.1-8.8)
9 longitudinal arm (9.1-9.16)
10 inner surface of the sheath body
11 inner profile
12 longitudinal bulge (12.1-12.8)
13 wave peak of the inner profile (13.1-13.8)
14 wave trough of the inner profile (14.1-14.8)
15 outer side of the sheath body
16 groove profile in the oblong implant section of the first implant
17 proximal transverse web (17.1-17.8)
18 distal transverse web (18.1-18.8)
19 wave trough of the groove profile 16
20 wave crest of the groove profile 16

The invention claimed is:

1. An implantable compensating sleeve for an endoprosthesis configured for application between an oblong implant section of a first implant and a second implant that encloses the oblong implant section of the first implant, the implantable compensating sleeve comprising:

a sheath having a sheath body and a passage extending from a proximal end of the sheath body to a distal end of the sheath body and configured to receive the oblong implant section of the first implant;

wherein the sheath body is divided by slits that extend into the sheath body in a longitudinal direction and originate alternately from the distal end of the sheath body and from the proximal end of the sheath body into meander-like segments, each meander-like segment comprising two longitudinal arms, and wherein the sheath body is radially expandable in at least one subsection;

wherein on an inner surface of the sheath body facing the passage, at least one bulge is provided, which extends in the longitudinal direction of one of the meander-like segments, thereby forming an inner profile that protrudes into the passage.

2. The implantable compensating sleeve according to claim 1, wherein the at least one bulge extends in the longitudinal direction of the meander-like segment and extends over both of the two longitudinal arms.

3. The implantable compensating sleeve according to claim 1, wherein bulges, including the at least one bulge, are provided on the inner surface of the sheath body facing the passage and form a circumferential inner profile, which is undulating in a cross-section of the compensating sleeve and has wave peaks and wave troughs.

4. The implantable compensating sleeve according to claim 3, wherein one of the wave peaks or wave troughs extends over the two longitudinal arms of a meander-like segment.

5. The implantable compensating sleeve according to claim 4, wherein the slits are alternately provided on a bottom of a wave trough and on a crest of a wave peak.

6. The implantable compensating sleeve according to claim 5, wherein the undulating circumferential inner profile has an axial symmetry with respect to a longitudinal axis of the compensating sleeve.

7. The implantable compensating sleeve according to claim 1, wherein an outer side of the sheath body is formed by an outer surface of the two longitudinal arms of a meander-like segment and is unprofiled.

8. The implantable compensating sleeve according to claim 7, wherein the inner profile is configured to complement a groove profile in the oblong implant section of the first implant.

9. The implantable compensating sleeve according to claim 1, wherein the compensating sleeve is made of a surgical steel, titan, or a titan alloy.

10. The implantable compensating sleeve according to claim 1, wherein the compensating sleeve is made of a biocompatible plastic material, in particular PEEK.

* * * * *